United States Patent [19]

Glass

[11] Patent Number: 5,128,322
[45] Date of Patent: Jul. 7, 1992

[54] AGENT FOR THERAPY

[75] Inventor: Mitchell Glass, Wilmington, Del.

[73] Assignee: Imperial Chemical Industries plc, London, England

[21] Appl. No.: 720,557

[22] Filed: Jun. 25, 1991

[30] Foreign Application Priority Data

Jun. 25, 1990 [GB] United Kingdom ............... 9014132

[51] Int. Cl.$^5$ ............... C07K 5/06; A61K 37/64; A61K 37/02
[52] U.S. Cl. ............... 514/19; 548/535; 548/538; 552/590
[58] Field of Search ............... 514/19

[56] References Cited

U.S. PATENT DOCUMENTS 4,910,190  3/1990  Bergeson ............... 514/19

Primary Examiner—Howard E. Schain
Assistant Examiner—P. L. Touzeau
Attorney, Agent, or Firm—Thomas E. Jackson

[57] ABSTRACT

There is provided a novel therapeutic agent for use in the prevention or treatment of hemorrhage associated with acute nonlymphocytic leukemia or its therapy, as well as a method of prevention or treatment of hemorrhage associated with acute nonlymphocytic leukemia or its therapy with the therapeutic agent, and a method of prevention or treatment of hemorrhage associated with acute nonlymphocytic leukemia or its therapy with the therapeutic agent in combination with one or more other agents indicated for the treatment of acute nonlymphocytic leukemia.

7 Claims, No Drawings

AGENT FOR THERAPY

This invention describes a novel agent for therapy and, more particularly, the use of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, in the prevention or treatment of hemorrhage associated with acute nonlymphocytic leukemia or its therapy. (Although the agent for therapy is named here as 1(RS), the invention described herein includes any ratio of the 1(R)-and 1(S)-isomers of the above named compound, or the pharmaceutically acceptable salts thereof.)

Hemorrhage, either spontaneous or associated with induction therapy (the therapeutic destruction of all abnormal white cells, and often substantially all white cells, by, for example, chemotherapy), is a serious and often fatal complication of acute nonlymphocytic (promyelocytic or myelocytic) leukemias. Bleeding during the first induction period is predictive of bleeding during subsequent inductions. The hemorrhagic complications have been associated with spontaneous or iatrogenic disseminated intravascular coagulation and extremely depressed blood levels of fibrinogen.

Accordingly, the present invention provides a novel agent for therapy for use in the prevention or treatment of hemorrhage associated with acute nonlymphocytic leukemia or its therapy in a mammal, especially a human, in need thereof which product comprises 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

As a further aspect of the invention, there is provided the use of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, for the manufacture of a medicament for the prevention or treatment of hemorrhage associated with acute nonlymphocytic leukemia or its therapy.

As another aspect of the invention, there is provided a method of prevention or treatment of hemorrhage associated with acute nonlymphocytic leukemia or its therapy in a mammal, especially a human, in need thereof with 4-(4-chlorophenylsulphonylcarbamoyl)-benzoyl-L-valyl-L-proline 1(RS)-(1-trifluoroacetyl-2-methylpropyl)amide, or a pharmaceutically acceptable salt thereof.

As yet another aspect of the invention, there is provided a method of treatment of acute nonlymphocytic leukemia with 4-(4-chloro-phenylsulphonylcarbamoyl)-benzoyl-L-valyl-L-proline 1(RS)-(1-trifluoroacetyl-2-methylpropyl)amide, or a pharmaceutically acceptable salt thereof, in combination with one or more other agents indicated for the treatment of acute nonlymphocytic leukemias. Such agents include, but are not limited to, antibiotics, corticosteroids, and anticancer agents.

Suitable pharmaceutically acceptable salts of 4-(4-chlorophenylsulphonylcarbamoyl)benzoyl-L-valyl-L-proline 1(RS)-(1-trifluoroacetyl-2-methylpropyl)amide (hereafter referred to as "the Compound") include, for example, those described in U.S. Pat. No. 4,910,190, for example, alkalai metal salts (such as sodium, potassium, calcium or magnesium salts), ammonium salts, and salts with organic bases affording a pharmaceutically acceptable cation. A preferred salt of the Compound for use for treatment of acute nonlymphocytic leukemias is, for example, a sodium or potassium salt.

The Compound and its production are described in U.S. Pat. No. ∝,910,190 where it was referred to as 3(RS)-[4-[(4-chlorophenyl)sulfonylaminocarbonyl]-phenylcarbonyl]-L-valyl-N-[3-(1,1,1-trifluoro-4-methyl-2-oxopentyl)]-L-prolinamide, but the name given hereinabove is now preferred. It is noted that Dess-Martin periodinane, described as the preferred oxidant and used in the final step for the production of the Compound in Examples 104 and 121, may in certain circumstances constitute an explosive hazard. Accordingly, it may be preferred to use an alternative oxidant for preparing the ketone from the corresponding alcohol. Alternative methods which may be useful include the use of oxalyl chloride, dimethyl sulfoxide and a tertiary amine (with the best results being obtained with 10–20 equivalents of oxidizing agent); the use of acetic anhydride and dimethyl sulfoxide; the use of chromium trioxide pyridine complex in methylene chloride; and the use of alkaline potassium permanganate solution. For example, the Compound may be obtained from the corresponding alcohol in approximately 60% yield using two equivalents of the latter oxidant.

In use, the Compound will generally be administered for the prevention or treatment of hemorrhage associated with acute nonlymphocytic leukemia or its therapy in the form of a conventional pharmaceutical composition, for example, as generally described in U.S. Pat. No. 4,910,190, and preferably as an injectable solution, given intravenously. A formulation providing a solution containing a concentration of 10 mg/mL of the Compound and suitable for use as an injectable solution is described below in Example 1.

In general, the therapeutic product will be administered to humans at a daily dose in the range of, for example, 5 to 7 mg/kg intravenously. However, it readily will be understood that it may be necessary to vary the dose of therapeutic product administered in accordance with well known medical practice to take account of the nature and severity of the hemorrhagic complications under treatment, concurrent therapy, and the age, weight and sex of the patient receiving treatment. It similarly will be understood that generally equivalent amounts of a pharmaceutically acceptable salt of the Compound also may be used.

The utility of the Compound, or a pharmaceutically acceptable salt thereof, in the prophylaxis or treatment of hemorrhagic complications associated with acute nonlymphocytic leukemia or its therapy may be demonstrated using standard clinical study protocols, for example as described below in Study A, in which improvement in clinical or biochemical parameters may be measured.

Study A in acute promyelocytic leukemia is a randomized, double blind, parallel study in 10 to 20 adult patients with prior hemorrhage assigned to receive 5 to 7 mg/kg/day of the Compound or vehicle (placebo) to be administered intravenously concurrently with induction therapy. A formulation as described in Example 1 may be used for the treatment group, and a similar formulation without the Compound for the vehicle (control) group. Clinical end points include mortality and severity of hemorrhage, analyzed using standard methods of statistical analysis. Biochemical indicia of a therapeutic effect may be obtained for measurements of fibrinogen fragments in blood and fibrin-split products.

The following non-limiting Example illustrates a typical formulation of the Compound for use in the method of treatment provided by the invention.

EXAMPLE 1

This example provides a formulation for 4-(4-chlorophenylsulphonylcarbamoyl)benzoyl-L-valyl-L-proline 1(RS)-(1-trifluoro-acetyl-2-methylpropyl)amide, listed as a "COMPOUND" which provides a strength of 10 mg/mL in phosphate-buffered saline and is suitable for a nebulizer solution or for an injectable solution. A corresponding PLACEBO formulation is also provided. The prepared solutions are preferably sealed in ampules of a convenient size, for example 5 mL, and stored with refrigeration until use.

| INGREDIENT | WEIGHT PER mL | |
|---|---|---|
| | 10.0 mg | PLACEBO |
| COMPOUND (1) | 10.0 mg | — |
| Dibasic Sodium Phosphate, Heptahydrate, USP | 11.97 mg | 10.74 mg |
| Monobasic Sodium Phosphate, Monohydrate, USP | 0.74 mg | 1.25 mg |
| Sodium Chloride, USP | 4.50 mg | 5.48 mg |
| 1N Sodium Hydroxide Solution or 0.05M Monobasic Sodium Phosphate Solution (2) | q.s. | q.s. |
| Water for Injection, USP q.s. ad | 1.0 mL (1.01 gm) | 1.0 mL (1.01 gm) |

(1) The nominal concentration of COMPOUND in this formulation is 10 mg/mL. A manufacturing adjustment is made for the drug substance purity.
(2) Added to adjust pH to 7.0–7.5

MANUFACTURING DIRECTIONS: AGENT FOR THERAPY

1. Charge approximately 90% of the required amount of Water for Injection, USP to a vessel equipped with a suitable agitation device, and connected to a heater/cooler circulation bath.
2. Adjust the temperature of the circulation bath to 30° C.
3. Charge with continuous stirring, the required amount of Dibasic Sodium Phosphate, Heptahydrate, USP and continue stirring until dissolved.
4. Charge very slowly with continuous stirring the required amount of COMPOUND.
5. Continue to stir for approximately 30 minutes until dissolved, then decrease the temperature of the circulation bath to 25° C.
6. Charge with continuous stirring the required amount of Monobasic Sodium Phosphate, Monohydrate, USP and continue stirring until dissolved.
7. Charge with continuous stirring the required amount of Sodium Chloride, USP and continue stirring until dissolved.
8. Measure the pH and adjust to 7.0 to 7.5 with 1 N Sodium Hydroxide Solution or 0.05 M Monobasic Sodium Phosphate Solution, if necessary.
9. Bring the batch to final weight (calculated from specific gravity of 1.01) with Water for Injection, USP.
10. Aseptically filter the bulk solution into a suitable, sterilized filling vessel. Aseptically fill and seal the ampules.
11. Leak test ampules and visually inspect for particulate matter and other defects.

MANUFACTURING DIRECTIONS: PLACEBO

The procedure listed above is carried out with the omission of steps 2, 4 and 5, and without the need for temperature control.

What is claimed is:

1. A method for the treatment of hemorrhage associated with acute nonlymphocytic leukemia or its therapy in a mammal in need thereof which comprises administering to said mammal an effective amount of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

2. A method as claimed in claim 1 wherein the pharmaceutically acceptable salt of the acid is selected from alkali metal and alkaline earth metal salts, ammonium salts, and salts with organic bases affording a pharmaceutically acceptable cation.

3. A method as claimed in claim 2 wherein the pharmaceutically acceptable salt is a sodium or potassium salt.

4. A method for the treatment of hemorrhage associated with acute nonlymphocytic leukemia or its therapy in a mammal in need thereof which comprises administering to said mammal an effective amount of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, where in addition one or more pharmacological agents indicated for the treatment of acute nonlymphocytic leukemia are administered to said mammal.

5. A method as claimed in claim 4 wherein the one or more other pharmacological agents are selected from the group consisting of antibiotics, corticosteroids and anticancer agents.

6. A method as claimed in claim 5 wherein the other pharmacological agent is an anticancer agent.

7. A method as claimed in claim 6 wherein the pharmaceutically acceptable salt is a sodium or potassium salt.

* * * * *